(12) United States Patent
Salzer (10) Patent No.: US 11,714,059 B2
(45) Date of Patent: Aug. 1, 2023

(54) ISOLATING INTERFERENCES IN ALKALINITY MEASUREMENT

(71) Applicant: Hach Company, Loveland, CO (US)

(72) Inventor: Corey Alan Salzer, Fort Collins, CO (US)

(73) Assignee: HACH COMPANY, Loveland, CO (US)

(*) Notice: Subject to any disclaimer, the term of this patent is extended or adjusted under 35 U.S.C. 154(b) by 159 days.

(21) Appl. No.: 17/132,527

(22) Filed: Dec. 23, 2020

(65) Prior Publication Data

US 2022/0196588 A1 Jun. 23, 2022

(51) Int. Cl.
*G01N 27/30* (2006.01)

(52) U.S. Cl.
CPC ......... *G01N 27/302* (2013.01); *G01N 27/301* (2013.01); *G01N 27/308* (2013.01)

(58) Field of Classification Search
CPC .. G01N 27/302; G01N 27/301; G01N 27/308; G01N 27/4167; G01N 27/44; G01N 31/164; G01N 33/182; G01N 31/16
See application file for complete search history.

(56) References Cited

U.S. PATENT DOCUMENTS

| | | | |
|---|---|---|---|
| 5,230,785 A * | 7/1993 | Yager | G01N 33/1813 204/405 |
| 5,597,463 A | 1/1997 | Birch et al. | |
| 2008/0257730 A1* | 10/2008 | Jiang | G01N 27/403 204/412 |

(Continued)

FOREIGN PATENT DOCUMENTS

| | | |
|---|---|---|
| EP | 0569908 A2 | 11/1993 |
| EP | 0569908 B1 * | 2/2002 |

(Continued)

OTHER PUBLICATIONS

Satoshi et al., English translation of KR20090079760A, 2009 (Year: 2009).*

(Continued)

*Primary Examiner* — Joshua L Allen
*Assistant Examiner* — Shizhi Qian
(74) *Attorney, Agent, or Firm* — Ference & Associates LLC (57) ABSTRACT

An embodiment provides a method for measuring a characteristic of an aqueous sample, including: introducing the aqueous sample to a titration region and a reaction region of a measurement device, wherein the titration region comprises a pH electrode and a protonator electrode contacting a first portion of an aqueous sample, wherein the reaction region comprises a counter electrode contacting a second portion of the aqueous sample; placing an electrolyte reservoir in a state of electrical continuity with the titration region and the reaction region, wherein the electrolyte reservoir comprises a reference electrode, wherein the volume of the electrolyte reservoir comprises a large volume of an electrolyte; and determining a characteristic of the aqueous sample by measuring an electrochemical characteristic between the reference electrode and at least one of: the pH electrode and the counter electrode. Other aspects are described and claimed.

20 Claims, 7 Drawing Sheets

(56) References Cited

U.S. PATENT DOCUMENTS

| | | | | |
|---|---|---|---|---|
| 2009/0145777 A1* | 6/2009 | Srinivasan | ............ | G01N 31/164 |
| | | | | 205/788.5 |
| 2010/0210026 A1* | 8/2010 | Hintz | .................... | G01N 31/16 |
| | | | | 422/77 |
| 2018/0224397 A1* | 8/2018 | Kroll | .................... | G01N 27/302 |
| 2019/0317044 A1* | 10/2019 | Rajasekharan | ...... | G01N 27/308 |

FOREIGN PATENT DOCUMENTS

| | | | | | |
|---|---|---|---|---|---|
| KR | 20090079760 A | * | 7/2009 | | |
| WO | WO1996001422 A1 | * | 1/1996 | | |
| WO | WO1998013675 A1 | * | 4/1998 | | |
| WO | WO-2015000769 A1 | * | 1/2015 | ........... | G01N 27/302 |

OTHER PUBLICATIONS

European Patent Office, International Search Report, dated Mar. 30, 2022, 5 pages.

P. Bergveld et al., "Development of a Microprocessor-Controlled Coulometric System for Stable pH Control", Analytica Chimica ACTA, Jan. 1, 1983, 5 pages, vol. 151, Elsevier Science Publishers B.V., Amsterdam, The Netherlands.

* cited by examiner

ISOLATING INTERFERENCES IN ALKALINITY MEASUREMENT

This application relates generally to electrochemical measurement of a sample, and, more particularly, to alkalinity measurement using electrochemical electrodes and isolating interferences.

BACKGROUND

Ensuring water quality is critical to the health and well-being of humans, animals, and plants, which are reliant on water for survival. Water quality parameters such as pH, oxygen, and other components may require monitoring. The monitoring of a sample is critical in a number of industries such as pharmaceuticals, biomedical, water supply, and other manufacturing fields. Water quality monitoring may allow for proper treatment of water or ensuring proper water quality for sensitive purposes, and allows for identifying the overall quality of the water. For example, one method to measure pH in an aqueous sample includes the use of electrodes, which require frequent maintenance and calibration of the pH measurement system.

BRIEF SUMMARY

In summary, one embodiment provides a method for measuring a characteristic of an aqueous sample, including: introducing the aqueous sample to a titration region and a reaction region of a measurement device, wherein the titration region comprises a pH electrode and a protonator electrode contacting a first portion of an aqueous sample, wherein the reaction region comprises a counter electrode contacting a second portion of the aqueous sample; placing an electrolyte reservoir in a state of electrical continuity with the titration region and the reaction region, wherein the electrolyte reservoir comprises a reference electrode, wherein the volume of the electrolyte reservoir comprises a large volume of an electrolyte; and determining a characteristic of the aqueous sample by measuring an electrochemical characteristic between the reference electrode and at least one of: the pH electrode and the counter electrode.

Another embodiment provides a measurement device for measuring a characteristic of an aqueous sample, including: a titration region comprising a pH electrode and a protonator electrode, wherein the pH electrode and the protonator electrode contact a first portion of an aqueous sample; a reaction region comprising a counter electrode, wherein the counter electrode contacts a second portion of the aqueous sample; an electrolyte reservoir in a state of electrical continuity with the titration region and the reaction region, wherein the electrolyte reservoir comprises a reference electrode, wherein the reference electrode contacts a large volume of electrolyte; and a memory storing instructions executable by a processor to: determine a characteristic of the aqueous sample by measuring an electrochemical characteristic between the reference electrode and at least one of: the pH electrode and the counter electrode.

A further embodiment provides a product for measuring a characteristic of an aqueous sample, including: a titration region comprising a pH electrode and a protonator electrode, wherein the pH electrode and the protonator electrode contact a first portion an aqueous sample; a reaction region comprising a counter electrode, wherein the counter electrode contacts a second portion of the aqueous sample; an electrolyte reservoir in a state of electrical continuity with the titration region and the reaction region, wherein the electrolyte reservoir comprises a reference electrode, wherein the reference electrode contacts a large volume of electrolyte; and a storage device having code stored therewith, the code being executable by the processor and comprising: code that determines a characteristic of the aqueous sample by measuring an electrochemical characteristic between the reference electrode and at least one of: the pH electrode and the counter electrode.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Electrochemical cells may be used to measure a characteristic of a sample. Using an electrochemical cell with a variety of electrochemical methods, which may include potentiometry, amperometry, and voltammetry, for example, can be employed for measurement of a characteristic of a sample. These characteristics may include pH, oxygen levels, conductivity, impedance, measurement of analyte in a solution, or the like. Such measurement of the characteristics of water or other solutions or samples is very common and allows for determination of the quality or other characteristics of the sample. Conventional three-electrode electrochemical cells may use a reference electrode, a counter electrode, and a working electrode. An electrochemical cell commonly employs the three electrodes placed in contact with the same sample solution, for instance, such that these electrodes can be used to determine a characteristic of a sample. For example, by maintaining or introducing an electrical potential or electrical current across two or more of the electrodes, a characteristic of the sample can be determined. An electrochemical cell may measure the concentration of an analyte, for example, hypochlorous acid, or the like, in an aqueous sample.

Conventional three-electrode electrochemical cells may be prone to problems. For example, electrodes may require periodic maintenance as redox reactions alter the condition of an electrode. Electrodes may need cleaning or reconditioning periodically to prevent drift and/or errors in electrochemical measurements. The reference electrode in a three-electrode cell may be problematic in obtaining long-term stable and accurate measurement of a sample. Often, three-electrode electrochemical cells or sensors will employ a reference electrode such as a conventional silver-silver chloride electrode or saturated calomel reference electrode. These types of reference electrodes utilize a half-cell potential established by an internal electrode bathed in a solution of known composition. For example, a silver-silver chloride reference electrode may be comprised of an inner silver electrode coated with silver chloride which is bathed in a chloride solution saturated with silver ions. The electrical conduit between the inner components of the reference electrode and a sample containing the counter and working electrodes of a common three-electrode cell is achieved by means of a restrictive conduit, or junction, between the inner solution of the reference electrode and the sample. The junction allows electrical continuity between the reference electrode and the other electrodes of the system without appreciable change of the inner fill solution of the reference electrode. Such reference electrodes can, however, be problematic in measurement of a sample as errors and maintenance issues can occur due to loss, contamination, or change in composition of the inner fill solution. Additionally, the inner fill solution can transfer across the junction and contaminate a sample, resulting in measurement errors. Further, the characteristics of the junction, such as ionic transfer impedance, can change due to fouling, plugging or damage resulting in drift and/or measurement errors.

Because of the above mentioned issues, the reference electrode in an electrochemical cell is frequently a cause of measurement errors. The maintenance or replacement of electrodes to maintain proper operation may be costly and time consuming. Pseudo-reference electrodes, often simply a silver chloride coated silver wire or platinum electrode in contact with a sample, are used in place of the standard half-cell reference electrodes mentioned above as a means to eliminate concerns with junctions and fill solutions. Unfortunately, the pseudo reference electrodes often lack sufficient potential stability, especially in situations with samples having variable composition. Eliminating issues associated with reference electrodes in electrochemical measurements would be advantageous in many electrochemical measurements.

For example, in a coulometric titration, separation of the cathode and anode may be preferred in order to mitigate issues associated with mixing of species produced at the counter electrode(s) which may interfere with the coulometric titration of interest. Additionally, a salt bridge comprised of an electrolyte solution contained in a tube by porous junctions on each end may be used to bridge between two separate compartments of an electrochemical cell with one compartment containing a working electrode and another containing a counter electrode. Additionally, in coulometric titration, the sample conductivity may impact the quality of the titration. In some instances, this may be mitigated by addition of an inert supporting electrolyte to the sample. However, this may be undesirable as the addition of a supporting electrolyte modify the activity of the analyte, for instance. The addition of supporting electrolyte may be problematic in practice of the measurement. In some cases, a salt bridge may provide inert electrolyte to the sample. What is needed is a bridging double junction reference electrode configuration as described herein.

Accordingly, the systems and methods described herein provide a technique for measuring a characteristic of an aqueous sample using an electrochemical cell. In an embodiment there may be three fluid regions which include a titration region, a reaction (counter or sample) region, and an electrolyte reservoir. The characteristic may be a pH of the aqueous sample. The regions may include gates or valves to control a fluid flow. The titration region may include a pH electrode and a protonator electrode. The pH electrode may be a boron doped diamond (BDD) electrode. The protonator electrode may be a boron doped diamond (BDD) electrode and/or may generate protons for the titration of the aqueous sample. The reaction region may include a counter electrode. The electrolyte reservoir may include a reference electrode. The titration region and the reaction region each contain a portion of an aqueous sample to measure. The electrolyte reservoir may contain an electrolyte. The titration region and the electrolyte reservoir may be in a state of electrical continuity through a junction. The reaction region and the electrolyte reservoir may be in a state of electrical continuity through a junction. The electrical continuity may be a junction. In an embodiment, the junction may be a porous junction, a membrane, or the like. The junction may be a ceramic, glass fiber, or the like. The volume of the electrolyte region may be large. In other words, the electrolyte volume may be such that it is of sufficient volume to prevent poisoning or contamination from a sample or reaction occurring in an adjacent region. For example, a fluidic separation of the titration region and the reaction region separates a contamination of a product produced at the counter electrode from the titration region In an embodiment, the state of electrical continuity comprises a bridged single junction, wherein a single junction provides continuity amongst the titration region, the reaction region, and the electrolyte reservoir.

For example, a coulometric titration may occur in the titration region of the device. Here, for example, a BDD protonator electrode can oxidize water to form H+ as a titrant for titration of bases (e.g., alkalinity determination). The titration may be monitored by a BDD pH electrode. Ions from an electrolyte solution in an Electrolyte Region separated from the titration region by a porous junction or membrane may supply inert ions for mitigating charge neutrality. At the same time, the ions of the electrolyte may provide a supply of inert ions to the reaction/counter/sample region where reduction may occur at the counter electrode as the other half of the reaction to the titration oxidation process. The electrolyte region may be separated from the reaction region by a porous junction or membrane. Sample may be introduced into the titration region where it may be captured via gates at the fore and aft of the titration region. Sample may be flowed into the reaction region and stopped during the titration process. After the titration is complete, both the titration region and the reaction region may be flushed with new sample. Alternatively, sample may be captured in the titration region for titration but sample may continuously be flushed through the reaction region during the measurement so as to continually flush away material formed at the counter electrode.

The electrolyte region may be a large volume so that the electrolyte within does not need to be replenished frequently. The reference electrode may be a standard reference electrode, thereby producing a 'bridged' double junction reference electrode design. Alternatively, a pseudo reference electrode may be used with an appropriate electrolyte to create a 'bridged' single junction reference electrode design; providing a simpler design but with a possibility of metal ions from the reference electrode contaminating the titration process.

The illustrated example embodiments will be best understood by reference to the figures. The following description is intended only by way of example, and simply illustrates certain example embodiments.

Figure 1:
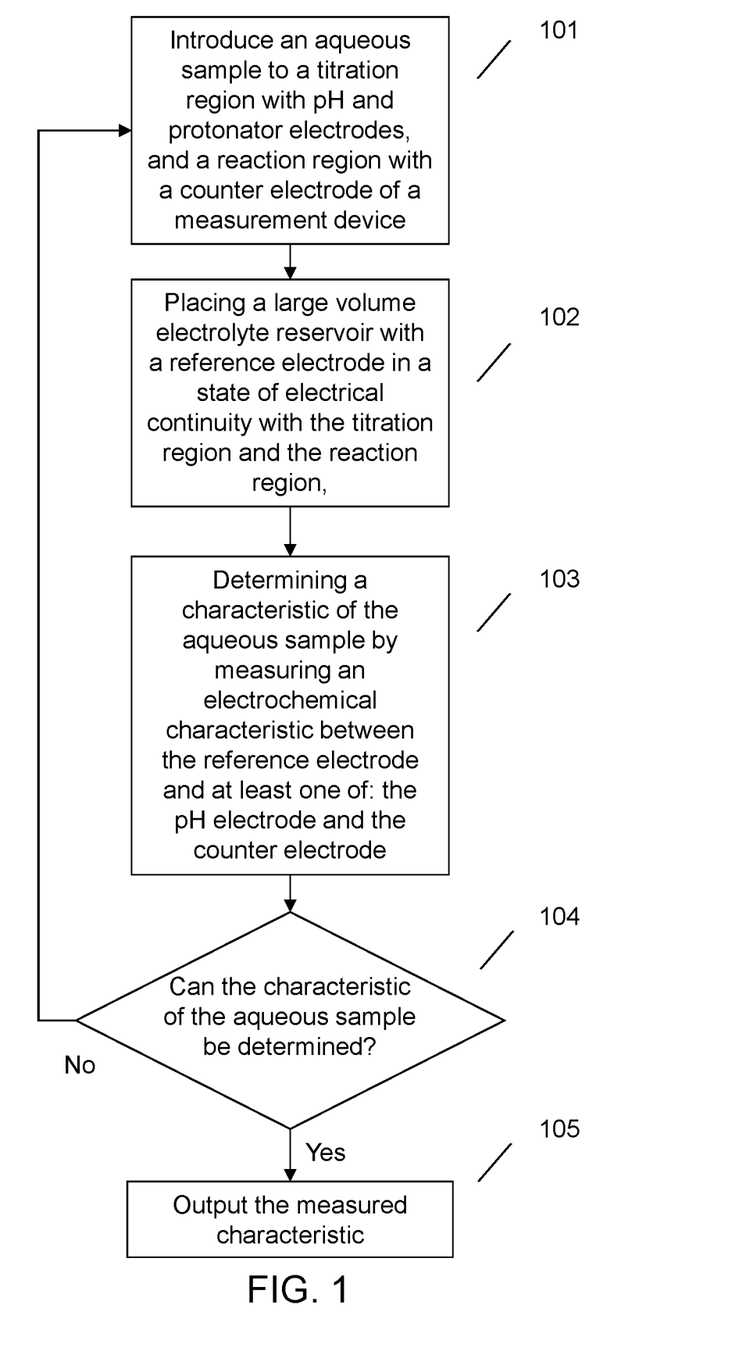
FIG. 1 illustrates a flow diagram of measuring a characteristic of a sample using an example embodiment.

As illustrated in FIG. 1, at 101, in an embodiment, an aqueous sample may be introduced to a titration region and a reaction region of a measurement device. A region may be a chamber, a cell, a vessel, or any structure capable of holding a volume of aqueous sample. The aqueous sample may be placed or introduced into a region manually by a user or using a mechanical means, for example, gravity flow, a pump, pressure, fluid flow, or the like. For example, a water sample for alkalinity testing may be introduced to a chamber by a pump, gravity flow, or the like with a valve or gate controlled the flow of aqueous sample. In an embodiment, there may be one or more regions in which the one or more method steps may be performed. In an embodiment, valves or the like may control the influx and efflux of the aqueous solution into or out of the one or more regions, if present. Once the sample is introduced to the measurement system, the system may measure the pH of the sample.

In an embodiment, the titration region may comprise at least one electrode. For example, the titration region may comprise a protonator electrode, a pH electrode, or both. See FIG. 2. In an embodiment, the protonator electrode may be a boron-doped diamond protonator electrode. In an embodiment, the pH electrode may be a boron-doped diamond pH electrode. The protonator electrode and pH electrode may be disposed or at least partially disposed in the aqueous sample in the titration region. The titration region may be in a state of electrical continuity with an electrolyte reservoir. The electrical continuity may be a junction. In an embodiment, the junction may be a porous junction, a membrane, or the like. The junction may be a ceramic, glass fiber, or the like. In an embodiment, the titration region may have an inflow and an outflow for the aqueous sample. The inflow and the outflow may comprise a gate or valve to control a flow of the aqueous sample. For example, a gate may be closed during a titration or measurement of an aqueous sample, and opened thereafter for a new volume of aqueous sample.

At 102, an electrolyte reservoir may be placed in a state of electrical continuity with the device. The electrolyte reservoir may be placed in electrical continuity with the titration region and the reaction region. The electrolyte reservoir may be referred to as a salt bridge. For example, the electrolyte reservoir may comprise a reference electrode. See FIG. 2. In an embodiment, the reference electrode may be a silver-silver chloride electrode (Ag/AgCl), a saturated calomel electrode (SCE), or the like electrode. The reference electrode may be disposed or at least partially disposed in the electrolyte in the electrolyte reservoir. In an embodiment, the electrolyte reservoir may be in a state of electrical continuity with both the titration region and the reaction region. The electrical continuity may be a junction. In an embodiment, the junction may be a porous junction, a membrane, or the like. The junction may be a ceramic, glass fiber, or the like. In an embodiment, the volume of the electrolyte reservoir may be a large volume. A large volume may be a volume greater than the volume of the titration region, the volume of the reaction region, or a combined volume of the titration region and the reaction region. In an embodiment, the volume of the electrolyte reservoir may be approximately one liter. For example, the volume of the electrolyte reservoir should be of a volume to keep the electrolyte solution as close to a composition as originally placed in the electrolyte reservoir after repeated cycles of titration and pH measurement. In this manner, the electrolyte would not require changing or maintenance as often as compared to a conventional configuration.

In an embodiment, the reaction region may comprise at least one electrode. For example, the reaction region may comprise a counter electrode. See FIG. 2. Thus the reaction region may be referred to as a counter reaction region or counter region. In an embodiment, the counter electrode may be of a material such as boron doped diamond (BDD) material, glassy carbon, graphite, titanium, gold, platinum, carbon, stainless steel, fluorinated tin-oxide or the like. The counter electrode may be disposed or at least partially disposed in the aqueous sample in the reaction region. The reaction region may be in a state of electrical continuity with an electrolyte reservoir. The electrical continuity may be a junction. In an embodiment, the junction may be a porous junction, a membrane, or the like. The junction may be a ceramic, glass fiber, or the like. In an embodiment, the reaction region may have an inflow and an outflow for the aqueous sample. The inflow and the outflow may comprise a gate or valve to control a flow of the aqueous sample. For example, a gate may be closed during a measurement of an aqueous sample, and opened thereafter for a new volume of aqueous sample.

In an embodiment, a separation of the titration and pH measurement from the counter electrode may provide advantages. For example, the configuration allows inert electrolyte to provide ion movement into the connected reaction regions to maintain charge neutrality and accommodate titration of different sample compositions through mitigation of ion migration effects. As another example, the configuration separates the anode and cathode to prevent contamination of the titration process by the products formed at the counter electrode, such as hydroxide ions produced at the counter electrode acting as a cathode during the titration. As a further example, the configuration may prevent contamination of the electrolyte solution as the sample in the counter electrode compartment may be continually flushed with sample or be flushed after each titration reaction thereby preventing or greatly minimizing contamination of the electrolyte by the products formed in the counter electrode region. As another example, the configuration may allow for a large volume of electrolyte to be incorporated into the cell as it is in a separate chamber, allowing for infrequent replenishment. As another example, a placement of the reference electrode in the electrolyte may reduce contamination of the reference electrode by sample components which may be referred to as poisoning.

Figure 2:
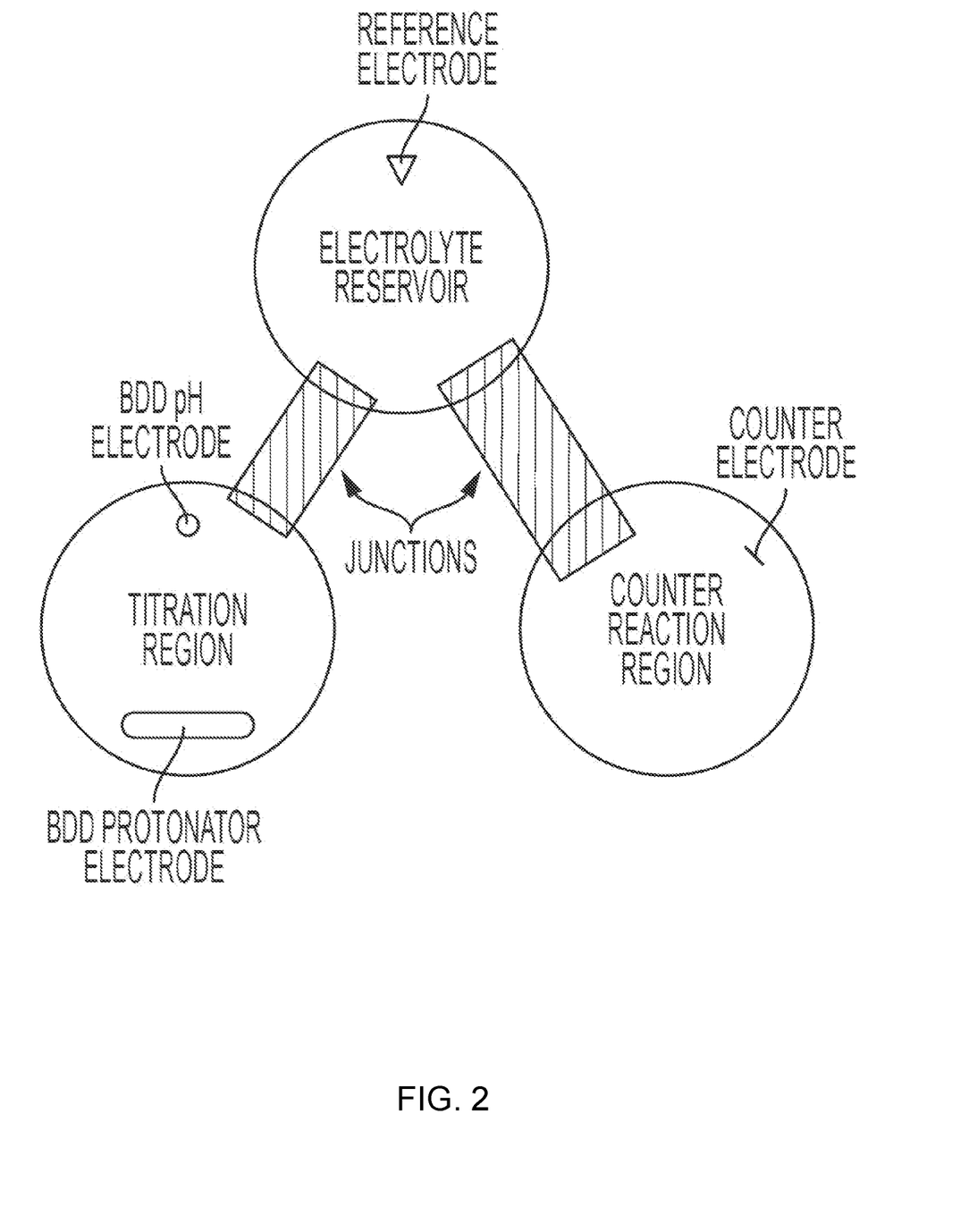
FIG. 2 illustrates an example embodiment of an electrochemical cell.
Figure 3:
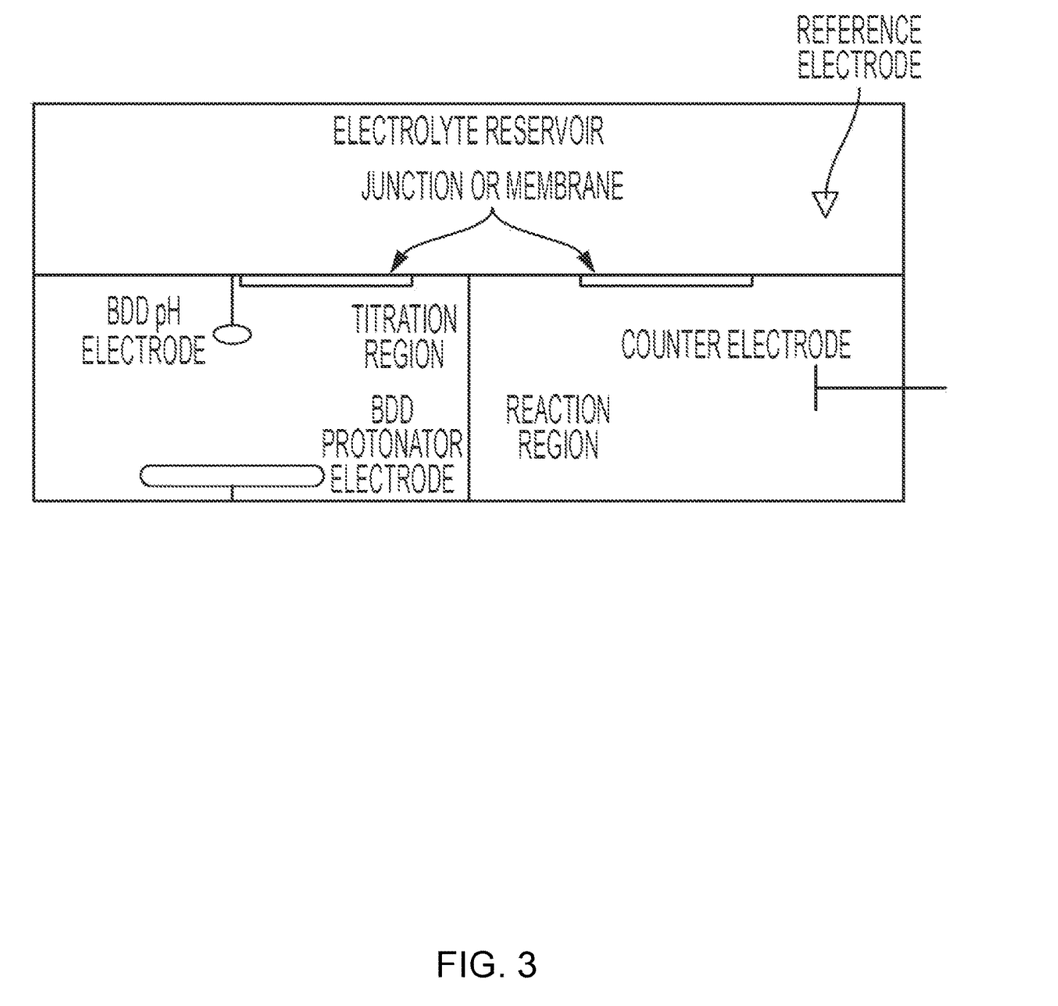
FIG. 3 illustrates another example embodiment of an electrochemical cell.
Figure 4:
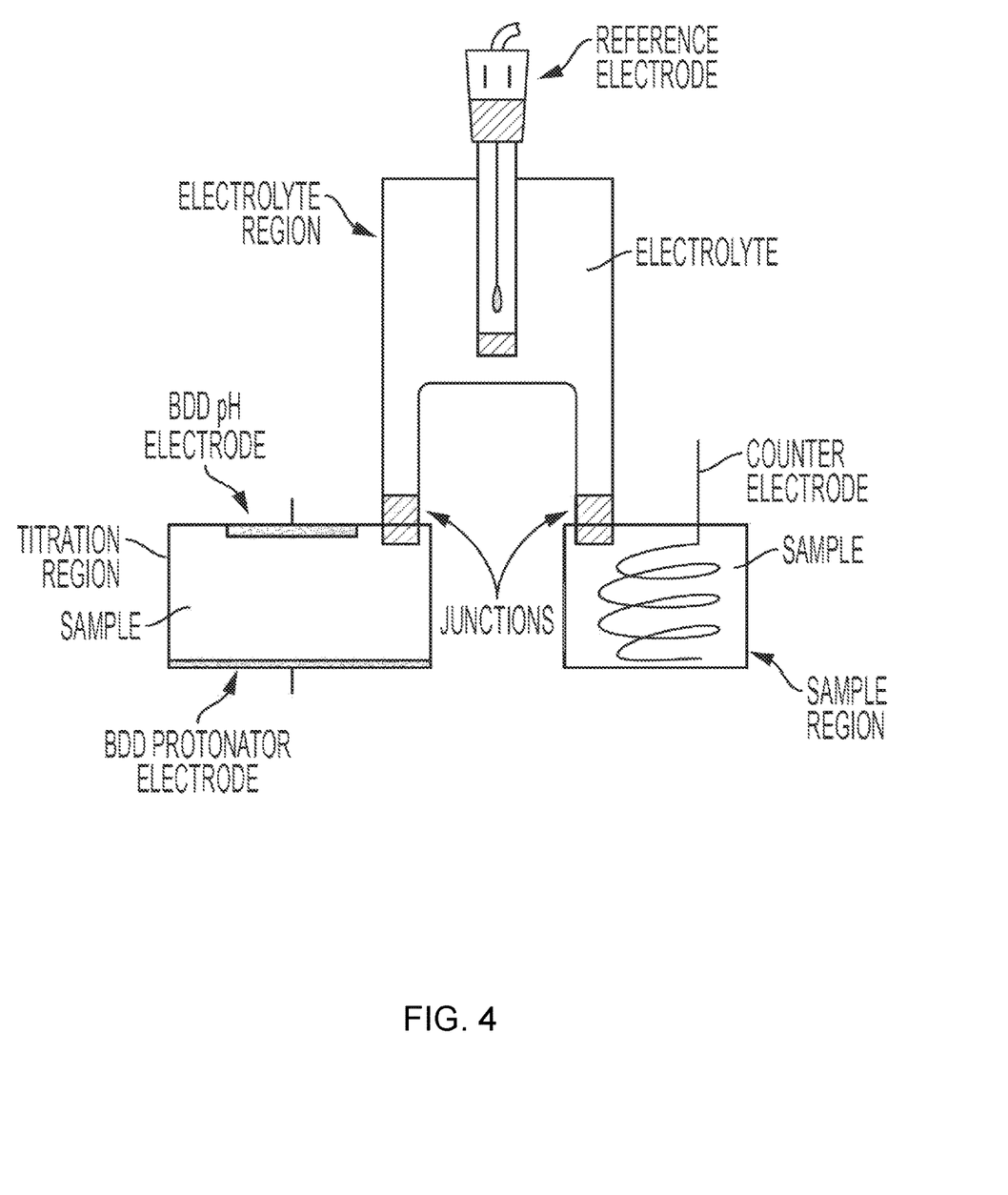
FIG. 4 illustrates another example embodiment of an electrochemical cell.
Figure 5:
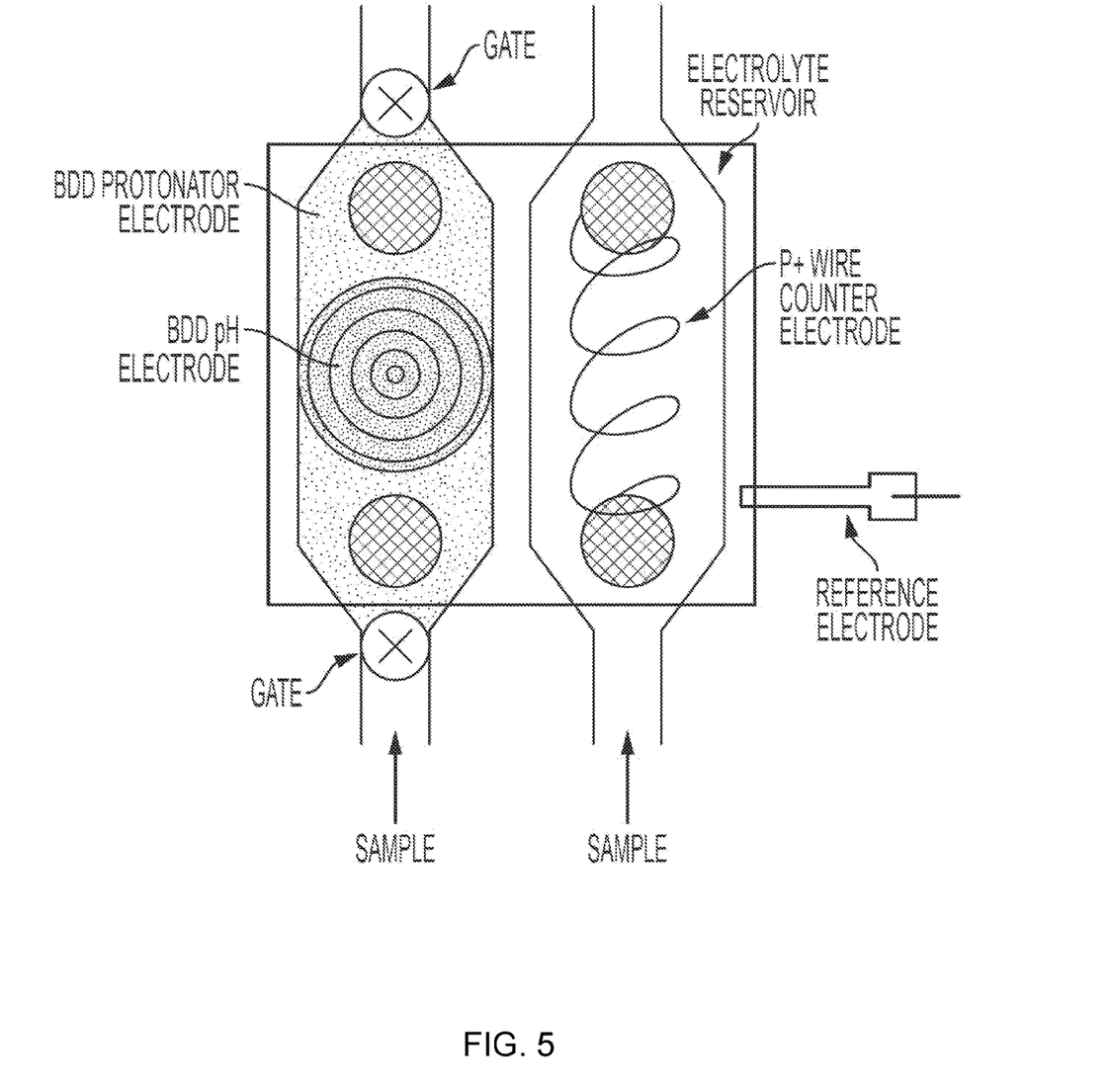
FIG. 5 illustrates another example embodiment of an electrochemical cell.
Figure 6:
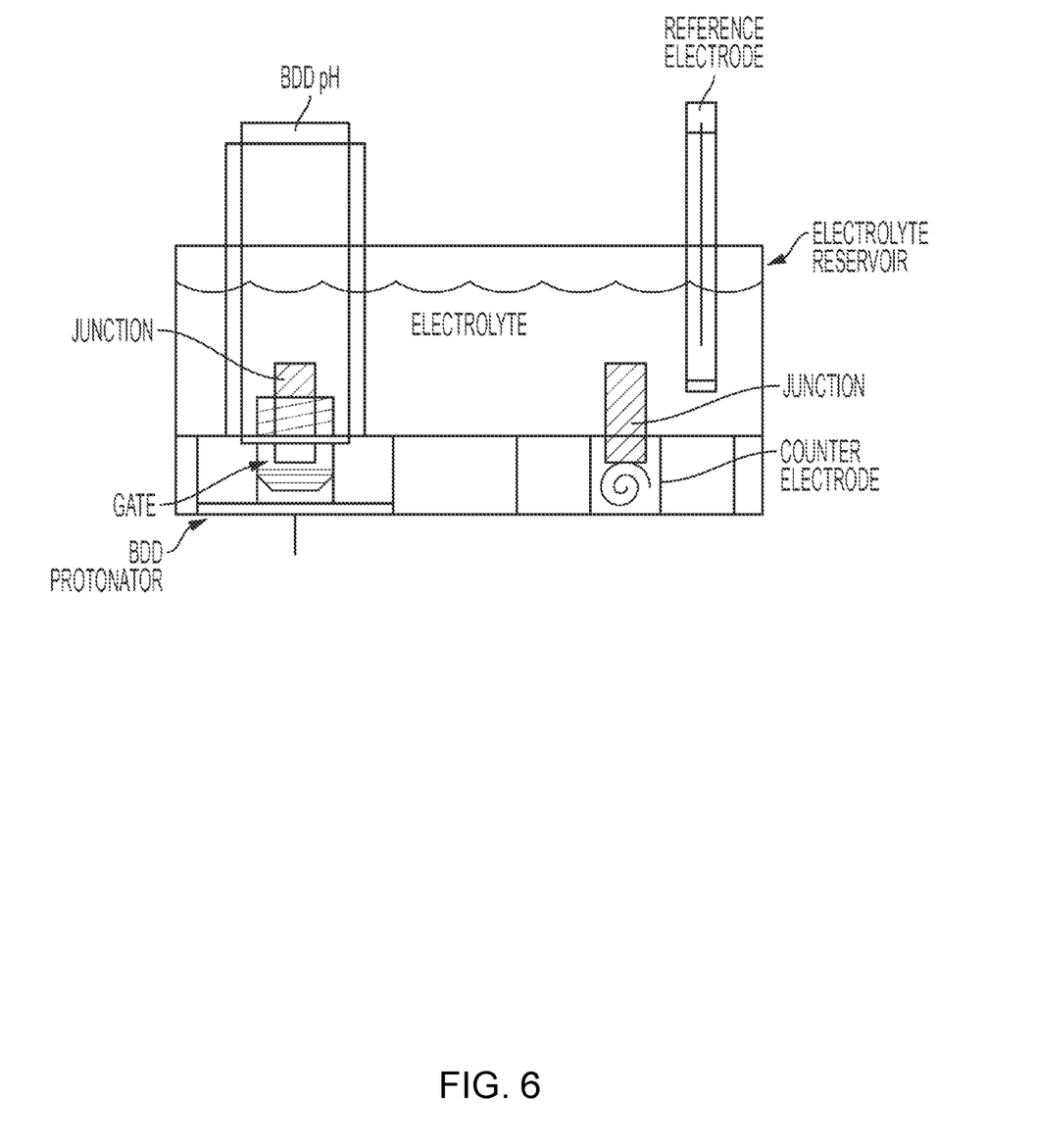
FIG. 6 illustrates another example embodiment of an electrochemical cell.

A simple illustration for a measurement device is illustrated in FIG. 2. However, other configurations are disclosed and contemplated. Referring to FIG. 3, in an embodiment, the titration region, reaction region, and electrolyte reservoir may be in a block configuration. For example, the electrolyte reservoir may sit upon the top of a titration region and the reaction region with junctions and various electrodes described herein. Referring to FIG. 4, in an embodiment, the electrolyte reservoir or region may be a volume with two protrusions extending down to a junction for each of the titration region and the reaction regions with various electrodes as described herein. Referring to FIG. 5, in an embodiment, the electrolyte reservoir may be a large volume with "tunnels" through which pass the aqueous sample for both the titration region and the reaction (counter) region with junctions and various electrodes described herein. Referring to FIG. 6, in an embodiment, the electrolyte reservoir may be a large tank volume with a titration region within the tank and a reaction region within the tank with junctions and various electrodes described herein.

At 103, in an embodiment, the method and system may determine a characteristic of the aqueous sample. In an embodiment, the characteristic may be a pH of the aqueous sample. Additionally or alternatively, the characteristic may be voltage, current, oxygen, ionic concentration, impedance, analyte concentration, analyte presence, or the like. In an embodiment, the method may measure an electrochemical characteristic between the reference electrode and at least one of: the pH electrode (working electrode) and the counter electrode. To make this determination, the system may, for example, use the current response between the working (for example a pH electrode) and counter electrodes to an applied potential between the working electrodes and the reference electrode to determine a resulting characteristic of the sample. For example, an amperometric approach for determining the concentration of a redox species in a sample may be used. The magnitude of the current between the working and counter electrode to application of a voltage between the reference electrode and the working electrode can be correlated to the concentration of a redox species in a sample solution. In another example, the pH electrode may monitor the pH of the sample during a titration. The protonator electrode may modify the pH of the sample by producing protons by oxidation of water in the sample. The pH electrode may monitor the titration of the sample to a pH end point. The alkalinity may be determined from the water oxidation process and measure of pH.

At 104, if the system cannot identify a characteristic of the sample solution, the system may continue to measure electrical responses from the electrodes of the system at 101 or any other step of the method. If the system cannot identify a characteristic of the aqueous sample, the system may continue to measure electrical responses from the electrodes of the system. For example, the system may acquire a new sample or try and retest the prior sample. Additionally, or alternatively, the system may trigger an alarm, shut down, alter flow control of the sample, or the like.

However, if, at 104, a characteristic of the sample may be determined, the system may output the pH or characteristic of a sample at 105. An output may be in the form of a display, storing the data to a memory device, sending the output through a connected or wireless system, printing the output, or the like. The system may be automated, meaning the system may automatically output the identified characteristic. The system may also have associated alarms, limits, or predetermined thresholds. For example, if a measured characteristic reaches a threshold, the system may trigger an alarm, adjust the characteristic of the aqueous sample, alter the flow of the sample, or the like. Data may be analyzed in real-time, stored for later use, or any combination thereof.

In an embodiment, the electrodes may be contacting the sample or electrolyte solution. For example, if a sample or electrolyte is introduced into a region having one or more electrodes, the sample or reference solution may at least partially cover the one or more electrodes. As another example, the one or more electrodes may be partially disposed within a region, with the other portion of the electrode outside the region. Thus, when a sample or reference solution is introduced into a region it only covers the portion of the electrode within the region. In an embodiment, the system may measure a property or characteristic of a sample in a sample region via application and or interrogation of an electrical signal across two or more electrodes. The electrical signal may be applied to or across one or more electrodes using, for example, a series of electrodes.

The various embodiments described herein thus represent a technical improvement to conventional electrochemical cells. Using the techniques as described herein, an embodiment may use a method and device for electrochemical cells. This is in contrast to conventional methods with limitations mentioned above. Such techniques provide a better method to construct and operate electrochemical cells.

Figure 7:
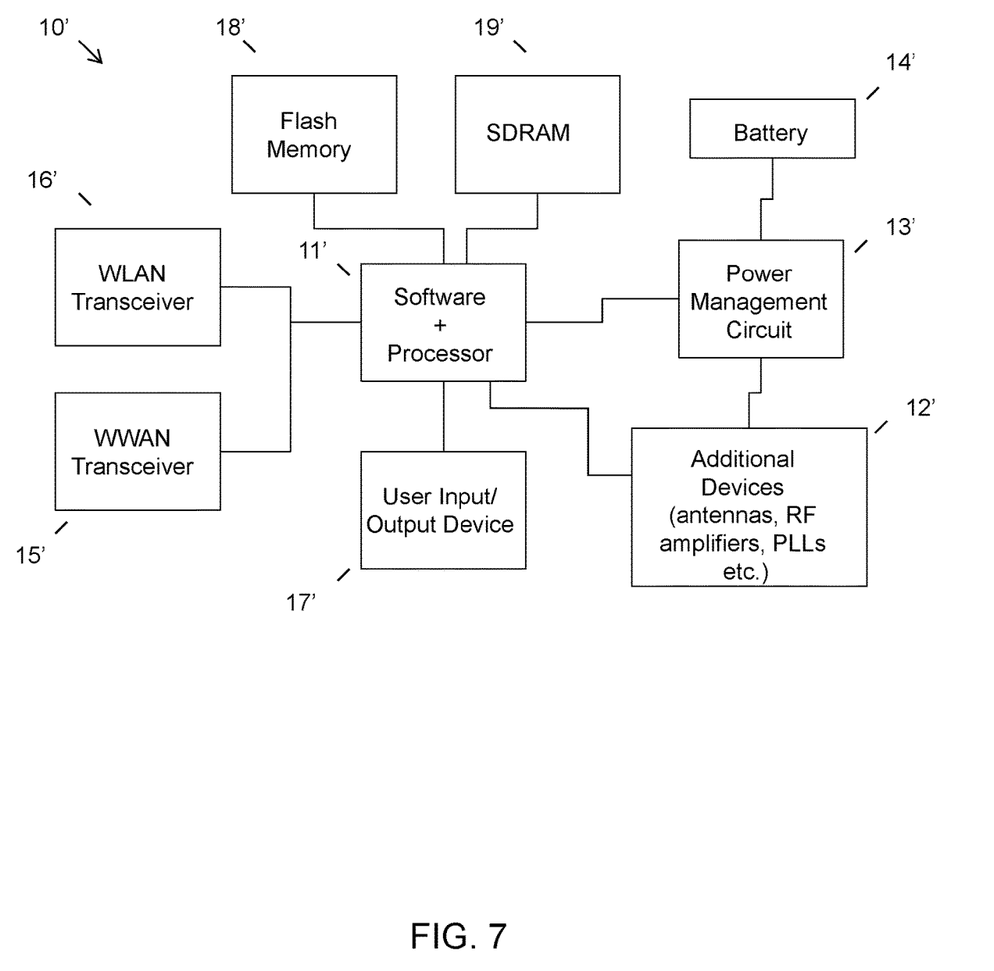
FIG. 7 illustrates an example of computer circuitry.

While various other circuits, circuitry or components may be utilized in information handling devices, with regard to electrochemical cells according to any one of the various embodiments described herein, an example is illustrated in FIG. 7. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment of an electrochemical cell.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring a characteristic of an aqueous sample, comprising:
   introducing the aqueous sample to a titration region and a reaction region of a measurement device, wherein the titration region comprises a pH electrode and a protonator electrode contacting a first portion of the aqueous sample, wherein the reaction region comprises a counter electrode contacting a second portion of the aqueous sample;
   placing an electrolyte reservoir in a state of electrical continuity with the titration region and the reaction region, wherein the electrolyte reservoir comprises a reference electrode, wherein the volume of the electrolyte reservoir comprises a volume of an electrolyte, wherein a path for a portion of the aqueous sample through the titration region and a path for another portion of the aqueous sample through the reaction region are parallel and fluidically separated from one another; and
   a memory storing instructions executable by a processor to determine the characteristic of the aqueous sample by measuring an electrochemical characteristic between the reference electrode and at least one of: the pH electrode and the counter electrode.

2. The method of claim 1, wherein the pH electrode comprises a boron-doped diamond pH electrode.

3. The method of claim 1, wherein the protonator electrode comprises a boron-doped diamond protonator electrode.

4. The method of claim 1, wherein the protonator electrode generates protons for titration of the aqueous sample.

5. The method of claim 1, wherein the titration region comprises at least one gate to stop flow of the aqueous sample.

6. The method of claim 1, wherein the reaction region comprises at least one gate to stop flow of the aqueous sample.

7. The method of claim 1, wherein the state of electrical continuity is selected from the group consisting of: a porous junction and a membrane.

8. The method of claim 1, wherein the state of electrical continuity comprises a bridge double junction, wherein a first junction is between the titration region and the electrolyte reservoir and a second junction is between the reaction region and the electrolyte reservoir.

9. The method of claim 1, wherein the state of electrical continuity comprises a junction for continuity amongst the titration region, the reaction region, and the electrolyte reservoir.

10. The method of claim 1, wherein a fluidic separation of the titration region and the reaction region separates a contamination of a product produced at the counter electrode from the titration region.

11. A measurement device for measuring a characteristic of an aqueous sample, comprising:

a titration region comprising a pH electrode and a protonator electrode, wherein the pH electrode and the protonator electrode contact a first portion of the aqueous sample;

a reaction region comprising a counter electrode, wherein the counter electrode contacts a second portion of the aqueous sample, wherein a path for a portion of the aqueous sample through the titration region and a path for another portion of the aqueous sample through the reaction region are parallel and fluidically separated from one another;

an electrolyte reservoir in a state of electrical continuity with the titration region and the reaction region, wherein the electrolyte reservoir comprises a reference electrode, wherein the reference electrode contacts a volume of electrolyte; and a memory storing instructions executable by a processor to:

determine the characteristic of the aqueous sample by measuring an electrochemical characteristic between the reference electrode and at least one of: the pH electrode and the counter electrode.

12. The measurement device of claim 11, wherein the pH electrode comprises a boron-doped diamond pH electrode.

13. The measurement device of claim 11, wherein the protonator electrode comprises a boron-doped diamond protonator electrode.

14. The measurement device of claim 11, wherein the protonator electrode generates protons for titration of the aqueous sample.

15. The measurement device of claim 11, wherein the titration region comprises at least one gate to stop flow of the aqueous sample.

16. The measurement device of claim 11, wherein the reaction region comprises at least one gate to stop flow of the aqueous sample.

17. The measurement device of claim 11, wherein the state of electrical continuity is selected from the group consisting of: a porous junction and a membrane.

18. The measurement device of claim 11, wherein the state of electrical continuity comprises a bridge double junction, wherein a first junction is between the titration region and the electrolyte reservoir and a second junction is between the reaction region and the electrolyte reservoir.

19. The measurement device of claim 11, wherein the state of electrical continuity comprises a junction for continuity amongst the titration region, the reaction region, and the electrolyte reservoir.

20. A product for measuring a characteristic of an aqueous sample, comprising:

a titration region comprising a pH electrode and a protonator electrode, wherein the pH electrode and the protonator electrode contact a first portion the aqueous sample;

a reaction region comprising a counter electrode, wherein the counter electrode contacts a second portion of the aqueous sample, wherein a path for a portion of the aqueous sample through the titration region and a path for another portion of the aqueous sample through the reaction region are parallel and fluidically separated from one another;

an electrolyte reservoir in a state of electrical continuity with the titration region and the reaction region, wherein the electrolyte reservoir comprises a reference electrode, wherein the reference electrode contacts a volume of electrolyte;

a processor; and a storage device having code stored therewith, the code being executable by the processor and comprising:

code that determines the characteristic of the aqueous sample by measuring an electrochemical characteristic between the reference electrode and at least one of: the pH electrode and the counter electrode.

* * * * *